United States Patent [19]

Terrell

[11] 3,932,667

[45] Jan. 13, 1976

[54] ETHER COMPOUND AS AN INHALATION ANESTHETIC

[75] Inventor: Ross C. Terrell, Plainfield, N.J.

[73] Assignee: Airco, Inc., Montvale, N.J.

[22] Filed: Apr. 5, 1973

[21] Appl. No.: 348,406

Related U.S. Application Data

[62] Division of Ser. No. 168,400, Aug. 2, 1971, Pat. No. 3,746,770.

[52] U.S. Cl. ............................................... 424/342
[51] Int. Cl. ............................................... A61k 27/00
[58] Field of Search .................. 424/342; 260/614 F

[56] References Cited
UNITED STATES PATENTS

| 3,346,448 | 10/1967 | Gilbert et al. | 424/342 |
| 3,663,714 | 5/1972 | Terrell | 424/342 |

OTHER PUBLICATIONS
Chemical Abstracts, 45:3321i (1951).

Primary Examiner—Jerome D. Goldberg
Attorney, Agent, or Firm—Roger M. Rathbun; Edmund W. Bopp; H. Hume Mathews

[57] ABSTRACT

Aliphatic ether compounds of the formula

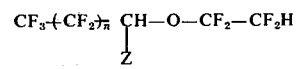

wherein Z is $CH_3$ or Cl, and n is zero when Z is $CH_3$ and is one when Z is Cl, are useful as inhalation anesthetics.

2 Claims, No Drawings

ETHER COMPOUND AS AN INHALATION ANESTHETIC

This application is a division of U.S. Pat. application Ser. No. 168,400, filed Aug. 2, 1971, now U.S. Pat. No. 3,746,770.

This invention relates to certain aliphatic ether compounds and their use in producing anesthesia in anesthetic-susceptible mammals.

The compounds of the present invention have the formula

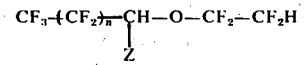

wherein Z is $CH_3$ or Cl, and $n$ is zero when Z is $CH_3$ and is one when Z is Cl. These compounds are mild anesthetics, the use of which is particularly desirable where very close control over the plane of anesthesia in the patient is desired or the amount of anesthetic administered is not to be regulated with great exactness. The compounds lend themselves to effective use as inhalant anesthetics in respirable mixtures containing life-supporting concentrations of oxygen, with or without other inhalation anesthetics, such as nitrous oxide. Administration of the compounds may be by any of the well known techniques for administering general inhalation anesthetics, for example by using the open drop, semi-closed, or closed systems.

The effective amounts of the compounds of this invention to be employed depend on the level of anesthesia to which the mammal is to be brought, the rate at which anesthesia is to be induced, and the length of time over which anesthesia is to be maintained. Minor volume percentages of the compound in oxygen can often be employed. The amount used should be sufficient to provide a significant anesthetic effect, but not so much as to produce unacceptable deleterious side effects. Vapor concentrations at which the compounds of this invention may often be used are about 4 to 15 volume percent, with the concentration actually employed depending on the choice of anesthetic; for instance, 1-methyl-1-hydroperfluoroethyl-2'-hydroperfluoroethyl ether may often be used in an amount of 5 to 15%, and 1-hydro-1-chloroperfluoropropyl-2'-hydroperfluoroethyl ether may often be used in an amount of 4 to 8%. The amount of anesthesia to be used can be regulated, starting with a small amount of the ether and gradually increasing the amount until the desired plane of anesthesia is reached. By then monitoring the physical reactions of the mammal, as is the usual procedure, the duration and plane of anesthesia can be readily controlled.

The compounds of this invention are also easily miscible with other organic liquids, including fats and oils, and have useful solvent properties, for example as solvents for fluorinated olefins and other fluorinated materials, such as fluoro waxes. The compounds of this invention may be used to prepare pastes and dispersions of such materials useful for coatings and the like, and may be used as degreasing agents. In the latter capacity, for example, the ether compounds of this invention can be used as solvents to remove grease from a metal surface that is to be painted.

The following examples illustrate the preparation of the compounds of the present invention.

EXAMPLE I

This example illustrates the preparation of 1-methyl-1-hydroperfluoroethyl 2'-hydroperfluoroethyl ether.

Tetrafluoroethylene was added to a solution of KOH (10 g.) in $CF_3(CH_3)CHOH$ in a 500 ml. stirred autoclave. The temperature was held at 70°C. and the pressure at 200–300 psi until no more tetrafluoroethylene reacted. Water was added and the product steam distilled and purified by fractional distillation to give $CF_3(CH_3)CHOCF_2CF_2H$.

Calculated for $C_5H_5F_7O$ : C,28.03; H,2.33;
Found : C,28.18; H,2.21.

This normally liquid compound has a boiling point of 70°C., a specific gravity of 1.4, a vapor pressure at 25°C. of 140 mm. Hg., and a not unpleasant odor. It is borderline as regards flammability.

EXAMPLE II

This example illustrates the preparation of 1-hydro-1-chloroperfluoropropyl 2'-hydroperfluoroethyl ether.

As the first step in the preparation on the compound 1,1-dihydroperfluoropropyl 2-hydroethyl ether, i.e. $CF_3CF_2CH_2OCF_2CF_2H$, was synthesized by the method employed in Example I, using $CF_3CF_2Ch_2OH$ instead of $CF_3(CH_3)CHOH$. The product had a boiling point of 68°C.

Calculated for $C_5H_3H_9O$ : C,23.9; H,1,2;
Found : C,24.22; H,1.45.

This intermediate ether was then chlorinated at 25° to 50°C. using chlorine gas in a glass reactor in the presence of incandescent light. The product, $CF_3CF_2CHClOCF_2CF_2H$, was isolated by preparative gas chromatography.

Calculated for $C_5H_2ClF_9O$ : C,21.1; H,0.7;
Found : C,21.1; H,0.88.

This normally liquid compound has a boiling point of 80°C., a specific gravity of 1.5, and a vapor pressure at 25°C. of 60 mm. Hg. This ether is nonflammable.

In order to determine the potency of the aliphatic ethers of the present invention as inhalation anesthetics in combination with oxygen, tests were carried out on mice. The compounds tested were at least 99.5% pure as determined by vapor phase chromatography. In the tests, the ether compound is administered to test mice by a standard procedure in which a measured quantity of the agent is placed in a laboratory jar and allowed to completely vaporize so as to give a calculated vapor concentration. The test mice are then quickly placed in the jar and observed. Anesthesia is determined by observing the righting reflex of the mice. Recovery time is measured beginning when the mice are transferred from the test jar to room air and ending when the mice are observed to be able to walk.

In such tests the 1-methyl-1-hydroperfluoroethyl 2'-hydroperfluoroethyl ether induced very light anesthesia in one minute 55 seconds at 5.0% vapor concentration. Recovery therefrom required 28 seconds. At 7.5% vapor concentration, induction time was shortened to 40 seconds and recovery time lengthened to one minute 55 seconds; marked excitement was observed during induction and recovery, and there was some twitching during anesthesia maintenance. At 10% concentration the induction was again accompanied by excitement but required only 20 seconds; recovery required 3 minutes 54 seconds. Respiration was depressed to about 32 per minute and jerky while the anesthesia was maintained in these 10% vapor concentration tests.

Using the 1-hydro-1-chloroperfluoropropyl 2'-hydroperfluoroethyl ether at 2.5% vapor concentration required an induction period of one minute 10 seconds and a recovery period of one minute 8 seconds. There was twitching, jumping, and rotating from induction through recovery. At 4.0% concentration the induction time was shortened to 35 seconds and recovery required one minute 42 seconds; depressed, shallow, gasping respiration and moving legs were observed during maintenance of the anesthesia, and the depressed respiration persisted during recovery.

While there has been described what are at present considered to be the preferred embodiments of the invention, it will be understood that various modifications may be made therein which are within the true spirit and scope of the invention.

I claim:

1. An inhalant anesthetic composition comprising an aliphatic ether compound of the formula $CF_3(CH_3)CH-O-CF_2CF_2H$ and oxygen in suitable proportions for use as an anesthetic.

2. A method of anesthetizing an anesthetic-susceptible mammal which comprises administering by inhalation to the mammal an anesthetically-effective amount of an aliphatic ether compound of the formula $CF_3(CH_3)CH-O-CF_2CF_2H$ while administering life-supporting amounts of oxygen.

* * * * *